(12) United States Patent
Lepot (10) Patent No.: US 9,630,745 B2
(45) Date of Patent: Apr. 25, 2017

(54) PACKAGING FOR THE STORAGE, PROTECTION AND TRANSPORT OF SYRINGES

(75) Inventor: Eric Lepot, Louvain-la-Neuve (BE)

(73) Assignee: Flexiways SPRL, Habay-la-Vieille (BE)

( * ) Notice: Subject to any disclaimer, the term of this patent is extended or adjusted under 35 U.S.C. 154(b) by 316 days.

(21) Appl. No.: 13/821,012

(22) PCT Filed: Sep. 16, 2011

(86) PCT No.: PCT/EP2011/066145
§ 371 (c)(1),
(2), (4) Date: Mar. 6, 2013

(87) PCT Pub. No.: WO2012/035155
PCT Pub. Date: Mar. 22, 2012

(65) Prior Publication Data
US 2013/0161225 A1    Jun. 27, 2013

(30) Foreign Application Priority Data

Sep. 17, 2010  (BE) .................................... 20100554
Mar. 30, 2011  (BE) .................................... 20110195

(51) Int. Cl.
*A61M 5/00*    (2006.01)
*B65D 25/00*   (2006.01)
*B01L 9/00*    (2006.01)
*B01L 9/06*    (2006.01)

(52) U.S. Cl.
CPC ............. *B65D 25/00* (2013.01); *A61M 5/001* (2013.01); *A61M 5/008* (2013.01); *B01L 9/00* (2013.01); *B01L 9/06* (2013.01); *B01L 9/54* (2013.01); *A61M 5/002* (2013.01); *A61M 2207/00* (2013.01); *B01L 2200/141* (2013.01); *B01L 2200/185* (2013.01); *B01L 2300/041* (2013.01)

(58) Field of Classification Search
USPC .................................................. 206/365, 366
See application file for complete search history.

(56) References Cited

U.S. PATENT DOCUMENTS

| 1,676,868 | A | * | 7/1928 | Petersen | ............ | B65D 43/0212 |
|---|---|---|---|---|---|---|
|  |  |  |  |  |  | 220/281 |
| 1,916,859 | A |  | 7/1933 | Heller |  |  |
| 2,818,979 | A |  | 1/1958 | Rose |  |  |

(Continued)

FOREIGN PATENT DOCUMENTS

| EP | 2072071 A1 | 6/2009 |
|---|---|---|
| EP | 1088566 A1 | 4/2013 |

(Continued)

*Primary Examiner* — Jacob K Ackun
(74) *Attorney, Agent, or Firm* — Christopher Casieri (57) ABSTRACT

A packaging unit (10) for the storage and/or transport and/or processing and/or support in a suspended vertical position, of objects (20), comprising a tray (30) which can retain a plurality of the objects in a vertical position, and a cover (32) which can cover the tray. According to the invention the cover (32) comprises an upper wall (34) and at least two flanks (24, 24') which extend downwards on two opposite sides of the upper wall, and are prolonged at their lower ends by fingers which can be placed below a lower surface of the tray (30), thus rendering the tray (30) and the cover (32) integral.

1 Claim, 11 Drawing Sheets

(56) References Cited

U.S. PATENT DOCUMENTS

| | | | | |
|---|---|---|---|---|
| 3,484,016 A * | 12/1969 | Turner | ................ | B65D 41/18 215/301 |
| 3,703,975 A * | 11/1972 | Wittemer | ............ | B65D 50/067 215/211 |
| 4,180,178 A * | 12/1979 | Turner | ............... | B65D 43/0212 215/317 |
| 4,380,292 A * | 4/1983 | Cramer | ........................ | 206/366 |
| 4,480,762 A * | 11/1984 | Thomas | ............... | B65D 50/045 215/216 |
| 4,500,006 A * | 2/1985 | Lafortune | ............ | B65D 50/045 215/224 |
| 4,733,778 A * | 3/1988 | Boeckmann | ........... | B65D 73/02 206/538 |
| 4,842,135 A * | 6/1989 | Borst | ................... | H05K 13/003 206/714 |
| 5,234,104 A * | 8/1993 | Schulte | ............... | H05K 13/003 206/341 |
| 5,249,679 A * | 10/1993 | Dondlinger | ................... | 206/366 |
| 5,449,077 A * | 9/1995 | Seidler | ................ | B65D 50/045 215/206 |
| 6,202,869 B1 * | 3/2001 | Sullivan | ............... | B65D 50/048 215/217 |
| 6,612,450 B1 * | 9/2003 | Buono | ............... | B65D 41/0414 215/225 |
| 7,600,639 B2 * | 10/2009 | Japuntich et al. | ............ | 206/366 |
| 9,139,350 B2 * | 9/2015 | Yeager | ................... | B65D 81/20 |
| 2003/0196922 A1 * | 10/2003 | Reaux | .......................... | 206/370 |
| 2005/0161355 A1 * | 7/2005 | Matthis et al. | ................ | 206/370 |
| 2011/0155599 A1 * | 6/2011 | Yakel et al. | ................... | 206/365 |
| 2012/0118903 A1 * | 5/2012 | Norton et al. | ................ | 220/755 |

FOREIGN PATENT DOCUMENTS

| | | |
|---|---|---|
| WO | 9414484 A2 | 7/1994 |
| WO | 9508392 A1 | 3/1995 |

\* cited by examiner

PACKAGING FOR THE STORAGE, PROTECTION AND TRANSPORT OF SYRINGES

This application is a 371 application of PCT/EP2011/066145, filed Sep. 16, 2011, which, in turn, claims priority of Belgian Patent Application Nos.: 2010/0554, filed on Sep. 17, 2010 and 2011/0195, filed on Mar. 30, 2011.

TECHNICAL FIELD

The present invention relates to a packaging unit for the storage, protection and transport of containers, and more particularly containers which are suspended in a vertical position such as, for example, syringes.

TECHNOLOGICAL BACKGROUND

At present, containers for medical products such as glass syringes are packed by the manufacturers in a form known as a "nest" and are supplied in sterile conditions. Supplying syringes in a "nest" format means supplying syringes which have been packaged on a plastic tray comprising mainly a support plate, known hereinafter as a nest tray, which is formed by a matrix of openings, with each of these openings supporting a syringe. This nest tray is typically supported by a plastic box known hereinafter as a nest box, which protects the syringes (see for example the product HYPAK® SCF®, Becton, Dickinson and Company of Franklin Lakes, N.J., USA). In addition, this packaging unit is covered by a cap, it is bagged, and is then ready for sterilization.

When the syringes are supplied in "nest" format to a pharmaceutical company, they must be handled in order to be filled one by one. After having removed the bag and the cap from each packaging unit manually, or by means of automated equipment, each nest tray is removed from its corresponding nest box, and the syringes are then filled one by one, line by line, or by series of several items. After the filling stage, it is necessary firstly to label each syringe for the purpose of defining the medical product contained, and secondly to inspect the syringes in order to detect any contamination of the product, as well as any cracks or scratches in the syringes. Other operations may be required, such as, for example, the addition of needle protectors or piston rods. The inspection is conventionally carried out by means of a system of optical sensors (or a camera) which inspect the syringes one by one. However, according to the habitual practice and for reasons of technical limitations (quantity of syringes, difficulties with labeling and/or inspecting the syringes placed in the central part of the nest tray, etc.), the syringes are firstly removed from the nest tray before being labeled and/or checked. Thus, when the syringes are finally labeled and/or checked, they are then again handled and stored, either directly in the nest box, without being stored on the nest tray, or in a different support, known hereinafter as a comb tray (see document U.S. Pat. No. 6,012,595 described hereinafter), which has multiple elongate fingers in order to keep the syringes suspended by their collars. It should be noted that after the labeling and/or inspection, the syringes are no longer reinserted in the nest tray, because it is more efficient and easier to store them in the comb tray which is purchased separately. A packaging unit of the nest type such as the product HYPAK® SCF®, is therefore not suitable for automated handling, since it requires complex machines. In addition, within the context of semi-automatic handling (with human assistance), it is difficult to exceed rates of more than 6000 syringes per hour. However, although on the one hand comb trays are preferable to nest trays for faster and easier storage of the syringes, on the other hand they are not suitable for the transport and storage of the syringes. In fact, when the comb trays are stored on one another in vertical columns, certain parts of the syringes are liable to be damaged or broken, because of their direct contact with the underneath of the packaging unit placed above. In order to avoid this problem, the comb trays must be placed in specific additional boxes, and provided with covers with an inner locking rim.

Specific boxes in which medical containers are arranged are known in the art, but, because of their structure, these are not suitable for all the automated steps of the production chain. Thus, a box with a structure which is too flexible and not rigid enough will for example prevent the satisfactory efficiency of a step of palletizing or de-palletizing, since these steps will be difficult for an automated system to handle.

Several sterilization modes are commonly used in order to treat the containers before they are filled, i.e. sterilization by steam, sterilization by a gas such as ETO, and sterilization by means of ionizing radiation. For sterilization by steam, it is necessary to overturn the containers, such that the condensation water which would be deposited inside the container can flow by means of gravity. During sterilization by ETO gas, it is also necessary to be able to overturn the containers in order to assist the discharge of residues of ETO gas, which is heavier than air. It is therefore necessary to provide means which retain the containers in their nest tray, in the overturned position.

The rules concerning safety of medical products require the presence of particles or dust to be reduced as far as possible. In known systems, friction between various components of the box during transport or storage can give rise to the creation of particles of this type. The rules also make it necessary to prevent the containers from being scratched or made fragile during impacts. It is also desirable to avoid human handling and even the presence of human operators in the vicinity of the containers during production. To summarize, the objective with packaging units for storage and transport is to protect the syringe against any damage or contamination during industrial operations of production, transport and/or storage.

PRIOR ART

The device for transport, storage and protection of syringes proposed by the applicant and described in document WO 2009/053434 is designed to fulfill the above-described requirements. In particular, it proposes a tray 30 with a plurality of rails 31 which form grooves 32 and permit easy insertion/removal of containers, and an upper wall 34 which retains the containers when the tray is overturned. However, the use of nest trays constitutes a widely established industrial standard. There is therefore a need for a solution to the above-described problems which is compatible with this industrial standard.

A device for the handling of objects is known from document EP 1088566. With reference to FIG. 10 of this document, a box 1 comprises a cover 4 and means for retaining and guiding syringes in the box. The cover 4 is articulated by means of a hinge, and makes it possible to prevent the syringes from coming out of the box during handling, in particular during the overturning for sterilization by steam. This device is useful for the sterilization step, but is not suitable for retaining syringes throughout the production chain, including during transport and storage. It is necessary to remove the containers from the original nest tray in order to put them in the traversing channels (element 26 in FIG. 1). The containers are then liable to touch one another, thus creating particles, and also causing a risk of making the containers fragile.

A nest tray cover is known from document EP 2072071. This cover 10 is placed on the base plate 2 of the nest tray 1 Control levers 17 make it possible to orient wings 16 in the grasping position, which has the effect of rendering the cover 10 integral with the nest tray, and thus permitting handling of the nest tray. However, this device is not designed for automatic processing: when the nest tray 1 is placed in a box 8 nothing is provided to permit grasping of the nest tray by a robot gripper. In addition, the control levers prevent the stacking of several boxes provided with a cover of this type. In fact, the lever extends from the plane formed by the rim of the cap. A cover of this type comprises numerous mobile parts, and is preferably made of stainless steel. Although this permits use of the cover for the sterilization step, its production cost does not allow it to be used on a larger scale during the transport and storage. Finally, the nests which are used in the industry have different formats: the nests for 160 containers have "orifices for finger passages 7" (also known as "ears") on the long side, whereas the nests which are designed for 100 containers have these orifices on the short side. This means that the handling means, such as the racks used in the autoclave, are different for each type of nest, i.e. for each format, in the entire production chain.

Document U.S. Pat. No. 2,818,979, which describes a device for retaining syringes, is also known. The device comprises a tray and a cover without lateral flanks, which can be retained together by means of a clip. Document WO 94/14484 describes a packaging unit comprising a tray of the comb type and a cover. The edges of the tray are arranged on a rim of the box, thus preventing the flanks of the cover from being placed below the tray.

SUMMARY OF THE INVENTION

The object of the invention is to eliminate the above-described disadvantages. In particular, its objective is to provide a packaging unit which permits immobilization of the containers in a nest tray, which thus prevents the risk of creation of particles, and permits sterilization by steam in the overturned position, whilst allowing easy handling by automatic means such as robots, and which is compatible with the industrial standards, irrespective of the format of the nest tray. The objective of the invention is also to provide packaging units which can be stacked.

According to a first aspect, the invention relates to a packaging unit for the storage and/or transport and/or processing and/or support in a suspended vertical position, of objects which have flanges. This packaging unit comprises a tray, which can retain a plurality of said objects in a vertical position, and a cover which can cover said tray. According to the invention, this cover comprises an upper wall and at least two flanks which extend downwards on two opposite sides of the upper wall, each of the flanks being prolonged at its lower end by fingers which can be placed below a lower surface of said tray, thus rendering the tray and the cover integral.

The upper wall advantageously has flexibility which makes it possible for it to be curved, such as to space one finger from an opposite finger, and thus to allow these fingers to be placed below the lower surface of said tray. The cover can thus be presented from above in a curved form, then released in order to be rendered integral with the tray.

The upper wall of the cover can have a plurality of passages. These passages can permit the circulation of gas and/or the filling of the containers.

The upper wall can also comprise ribs on its lower surface. These ribs, which ensure the rigidity, are preferably parallel to the flanks, and preferably above the collars.

According to a second preferred embodiment of the invention, the upper wall comprises on its lower surface at least two support walls which extend downwards, parallel to the flanks and situated on the inner side of the latter. These support walls make it possible to place the cover on the tray, preferably at the height of the inverted "U" of the step, and thus facilitate the stacking of several packaging units.

According to a third preferred embodiment of the invention, the flanks are interrupted, and portions of tube are placed in these interruptions. These portions of tube make it possible to position the cover on the tray.

The packaging unit according to the invention can also comprise a box with an upper opening, a base, lateral walls, and a step formed between said upper opening and said lateral walls in order to support said tray. According to the invention, this step comprises a rib in the form of an inverted "U" which extends on the inner portion of said step. This rib provides a release which allows the cover to be positioned on a tray arranged in a box.

First means for immobilization of the tray in a box provide for the step to comprise at least one centering pin and the tray to comprise at least one cut-out or one corresponding round hole.

The pins advantageously have a frustoconical form. The cut-out(s) can have the form of a "V".

According to other means for immobilization, the inner surface of the upper lateral wall of the box comprises a vertical rib. This rib guides and blocks the tray in the box.

The box comprises an upper rim which can advantageously comprise an opening in at least one angle of the box. This opening makes it possible to eliminate condensation and ETO, and also makes it possible to raise a cap which may be glued on.

According to a second aspect, the invention relates to a process for storage and/or transport and/or processing and/or support in a suspended vertical position, of objects which have flanges, comprising the use of a tray which can retain pluralities of said objects in a vertical position, and a cover which can cover said tray, comprising the steps of:
 providing a cover comprising an upper wall and at least two flanks which extend downwards on two opposite sides of the upper wall, each of the flanks being prolonged at its lower end by fingers which can be placed below a lower surface of said tray;
 grasping of said cover by grasping means;
 imposition by the grasping means of curvature on the upper wall of the cover, thus spacing two flanks from one another;
 positioning of the cover facing the tray;
 releasing of said curvature, the fingers thus rendering the tray and the cover integral.

Preferably, the step of positioning of the cover facing the tray is carried out with the tray being supported in a box.

According to a third aspect, a method is provided for separation and/or assembly of the elements which constitute one or a plurality of packaging units according to the present invention. Each packaging unit comprises a tray which can retain a plurality of objects provided with flanges in a vertical position, a cover which can cover said tray, and a box which supports said tray. Said method for separation and/or assembly comprises the steps of:

grasping of one or a plurality of packaging units according to the invention by an automatic grasping means;

separation of said box from the assembly formed by the tray covered with the cover, by means of said automatic grasping means;

separation of said tray containing said objects from said cover by means of said automatic grasping means;

processing of said tray;

subsequent reassembly of said tray with said cover, then of the assembly thus formed with said box by means of said automatic grasping means.

Preferably, the step of processing of said tray can consist of the removal of the objects retained in a vertical position in said tray, in order to make these objects available. Alternatively the step of processing of said tray can consist of the arrangement of objects provided with flanges in said tray. Said tray can be a tray of the nest type, or it can be in the form of a comb.

Preferably, the automatic grasping means can be a grasping robot. Said grasping robot can be provided with a single grasping unit. Said grasping unit can separate and assemble the box, the tray and the cover for the packaging units according to the present invention.

Preferably, said method can use a cover comprising an upper wall and at least two flanks which extend downwards on two opposite sides of the upper wall, each of the flanks being prolonged at its lower end by fingers which can be placed below a lower surface of said tray, thus rendering the tray and the cover integral, and said flanks are interrupted, and portions of tube are placed in these interruptions.

Preferably, said method for separation can be carried out with at least two packaging units simultaneously. In particular, said method for separation can be carried out with two packaging units simultaneously. Said method according to the invention thus permits the separation or assembly of the component elements of a packaging unit according to the invention in a production chain, by means of an automatic grasping means. The method is facilitated by means of the technical characteristics of the cover as previously described. In particular, said method is favourable when the cover is provided with flanks on two of its sides, said flanks being interrupted and arranged on portions of tube. Specifically, a method of this type can permit the automatic grasping of the packaging unit in optimum conditions without risk of deterioration of said objects contained in the tray, even in a vertical position. By means of the characteristics of the cover according to the invention, an automatic grasping means provided with a single grasping unit can assemble or separate the packaging unit assembly. Said method thus has numerous advantages which can be applied in the field of the internal (or transit) logistics of a company, i.e. all of the operations which permit the conveying, transfer and handling of materials and products.

BRIEF DESCRIPTION OF THE DRAWINGS

FIGS. 1b and 1c are general drawings of a tray and a cover of a packaging unit according to the invention. In FIG. 1b, the cover is curved for the purpose of its insertion on the tray. In FIG. 1c the cover is placed on the tray.

FIGS. 2c and 2d are enlarged views of the details indicated by the circles "C" and "D" in FIG. 2a.

DETAILED DESCRIPTION OF THE INVENTION

The invention is described hereinafter by examples, in relation with the figures, in which elements which are identical or corresponding have the same reference numbers.

Figure 1A:
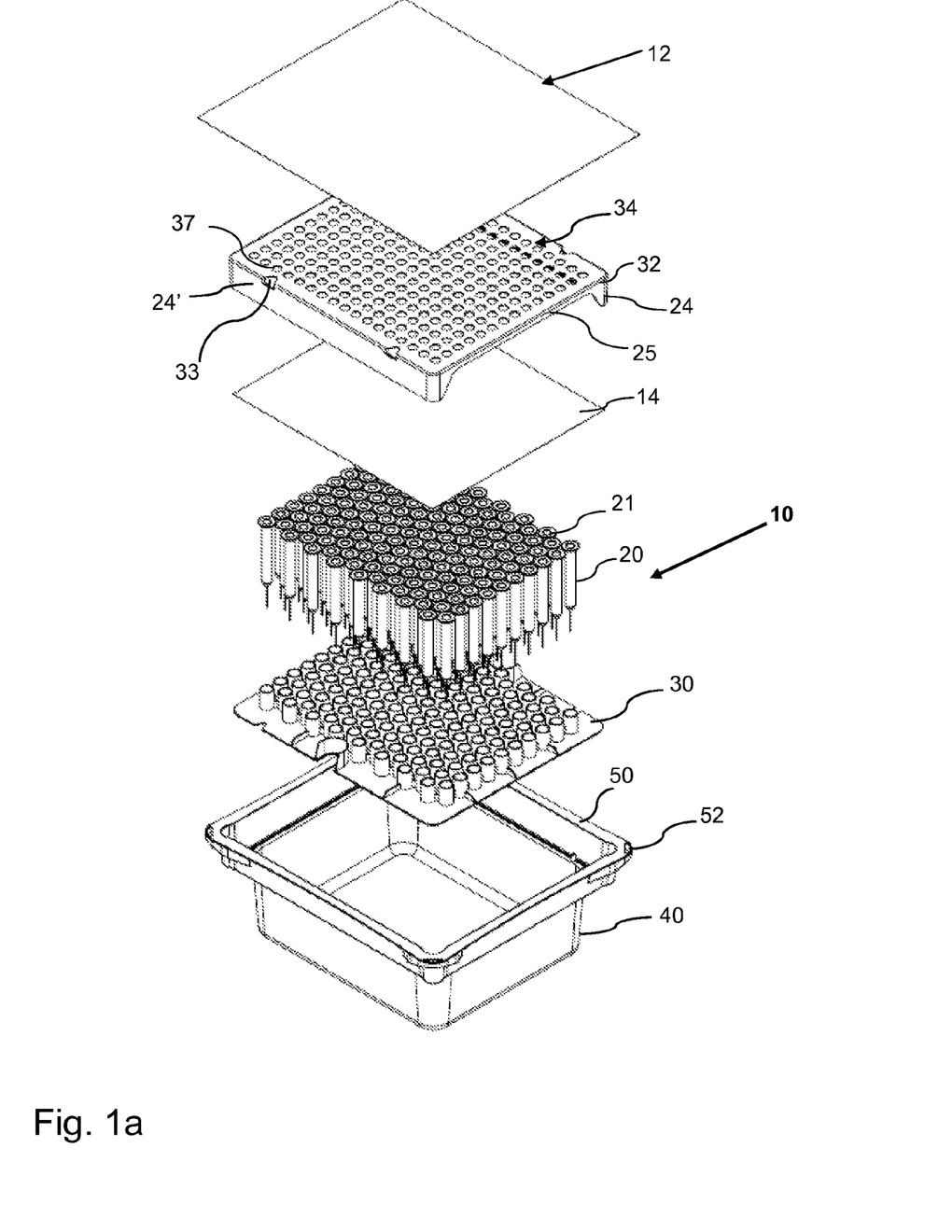
FIG. 1a is a view in exploded perspective of components of a packaging unit according to a first embodiment of the invention.

FIG. 1a is a view in exploded perspective of components of a packaging unit 10 according to a first embodiment of the invention, and represents in succession, from top to bottom, a cap 12 which can be used to close the packaging unit, a cover 32, an optional separation sheet 14, an assembly of syringes 20 with flanges 21, a nest tray 30 and a box 40.

According to the invention, the cover 32 has an upper wall 34, and flanks 24, 24' which extend downwards from two opposite sides of the upper wall 34. The tray represented in the following examples is a nest tray. The invention can however also be used in conjunction with a comb tray. Hereinafter, the generic term "tray" will be used to designate these two types of trays.

Figure 1B:
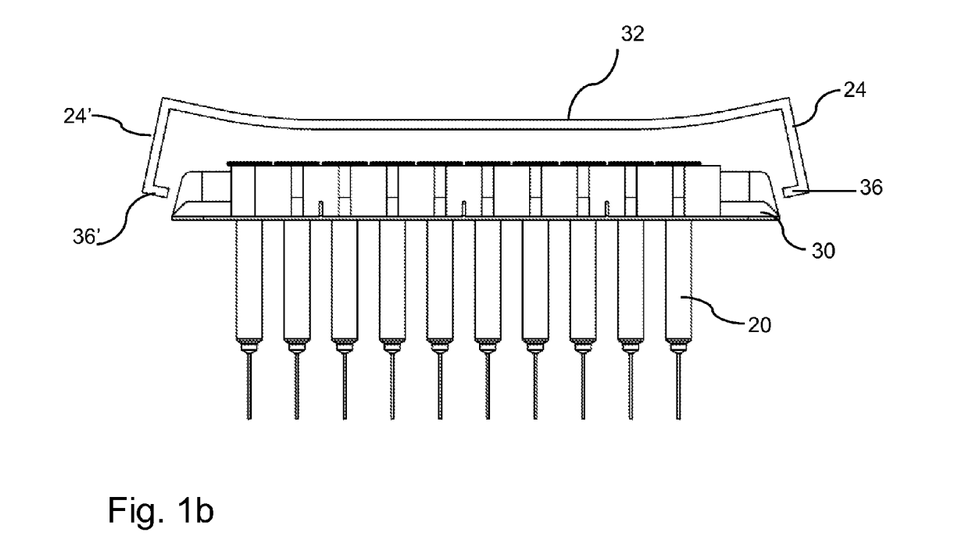
Figure 1C:
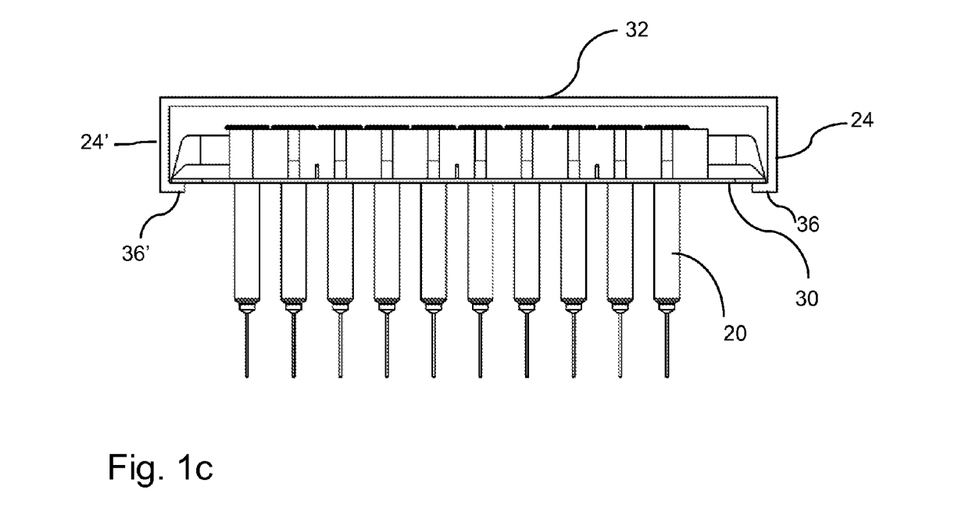

FIGS. 1b and 1c represent a method for rendering the cover 32 integral with a tray 30. The assembly of a cover 32 on a tray 30 and removal from it can be carried out very easily by automatic means: for example, a grasping tool of a robot comprises a plurality of suckers which are applied to the upper surface of the upper wall 34. The grasping tool imparts curvature in the form of a "U" on the upper wall 34, as represented schematically in FIG. 1b. The opposite fingers 36, 36' are then slightly spaced, and can be placed below the tray 30. The grasping tool then releases the cover 32, which regains its flat form, and is then rendered integral with the tray 30. The same operations in the opposite direction make it possible to separate the cover 32 from the tray 30. As a variant, the cover 32, which is not curved, can be slid longitudinally on the tray. This securing mode is advantageous when the cover is in the form of a slide, or has a form which can be extruded.

Figure 2A:
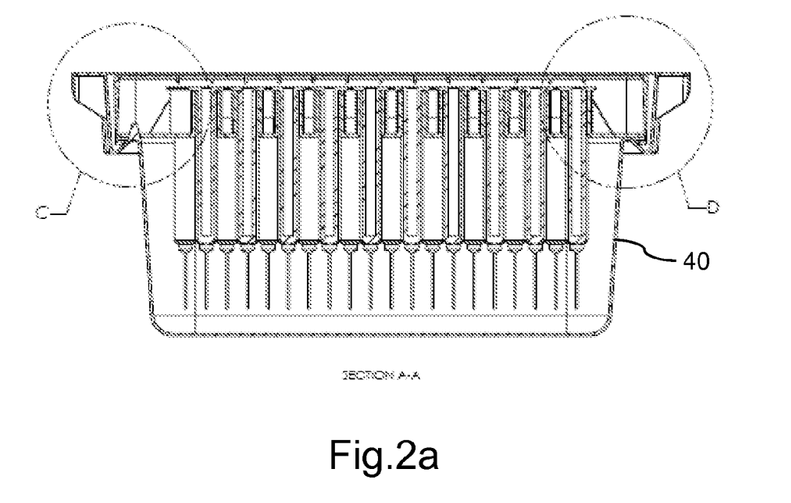
FIGS. 2a and 2a are respectively a view in cross-section along the plane AA indicated in FIG. 2b, and a plan view of this same packaging unit.

FIG. 2a represents the cover of a first embodiment of the invention, and indicates how the horizontal fingers 36 and 36' which prolong the flanks 24, 24' are inserted below the lower surface of the tray 30. These horizontal fingers extend substantially along the entire length of the flanks 24, 24'. The cover 32 can be made by molding or also by extrusion of a polymer such as polycarbonate. The syringes 20 are supported by their flanges 21, such that their needles are suspended above the base 43 of the box 40. The box 40 comprises in a known manner a step 45 which is designed to support the tray 30 at an appropriate height. According to a preferred embodiment of the invention, this step can comprise, on its part situated towards the interior of the box, a rib in the form of an inverted "U" 41, around all or part of the periphery of the step 45. This rib 41 has the effect that the peripheral ends of the tray 30 are free, and therefore the fingers 36, 36' can be placed below the tray 30, even when the latter is positioned in the box: it is not necessary to raise the tray 30 in order to put the cover 32 in place.

Figure 2B:
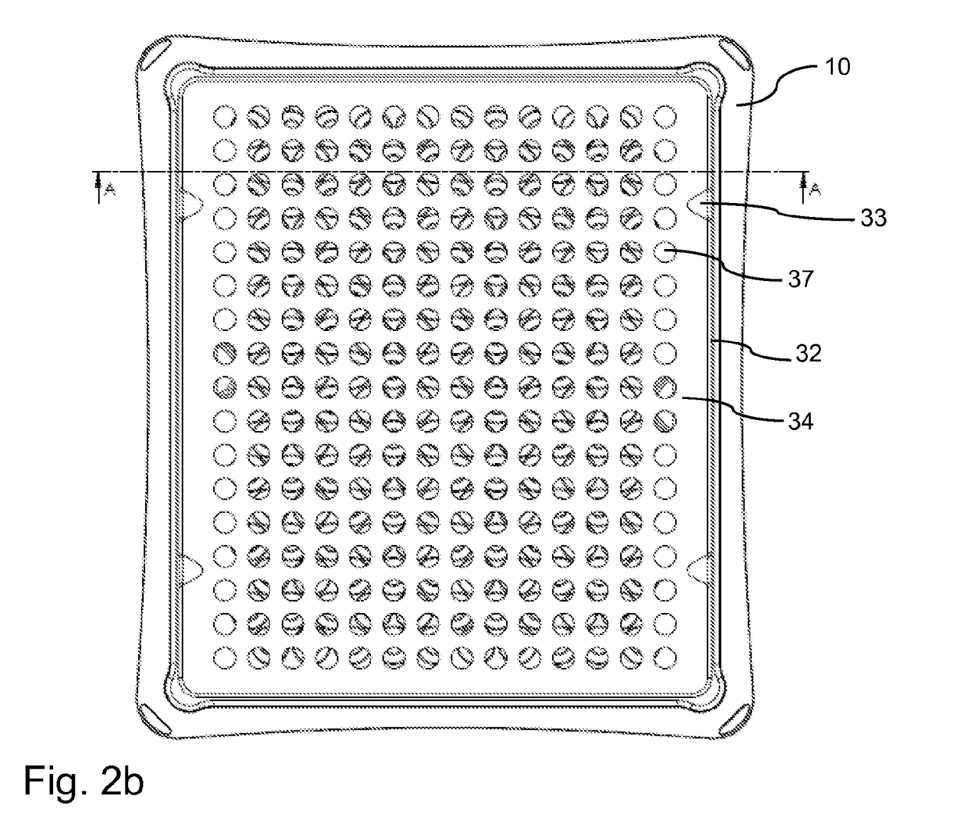

FIG. 2b represents in particular openings 37 which are provided in the upper wall 34 of the cover 32. These openings 37 permit the circulation of the steam or gas during the sterilization. According to a preferred embodiment, they are placed above openings in the containers 20, and thus permit filling and/or plugging of the containers. Centering cut-outs 33 can be provided in the upper wall 34 of the cover 32. These centering cut-outs can be used by automatic grasping means in order to position the cover with precision during industrial operations.

Figure 2C:
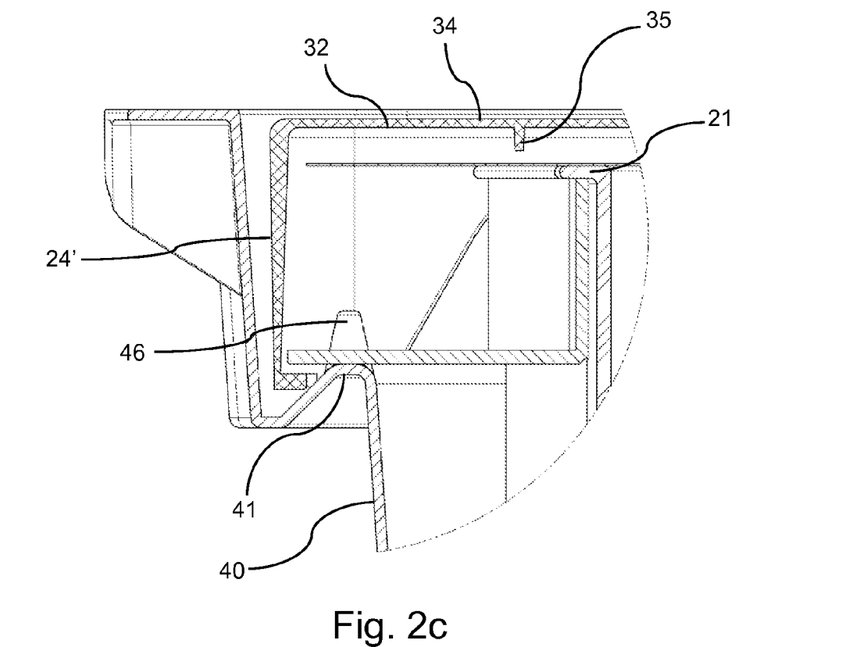
Figure 2D:
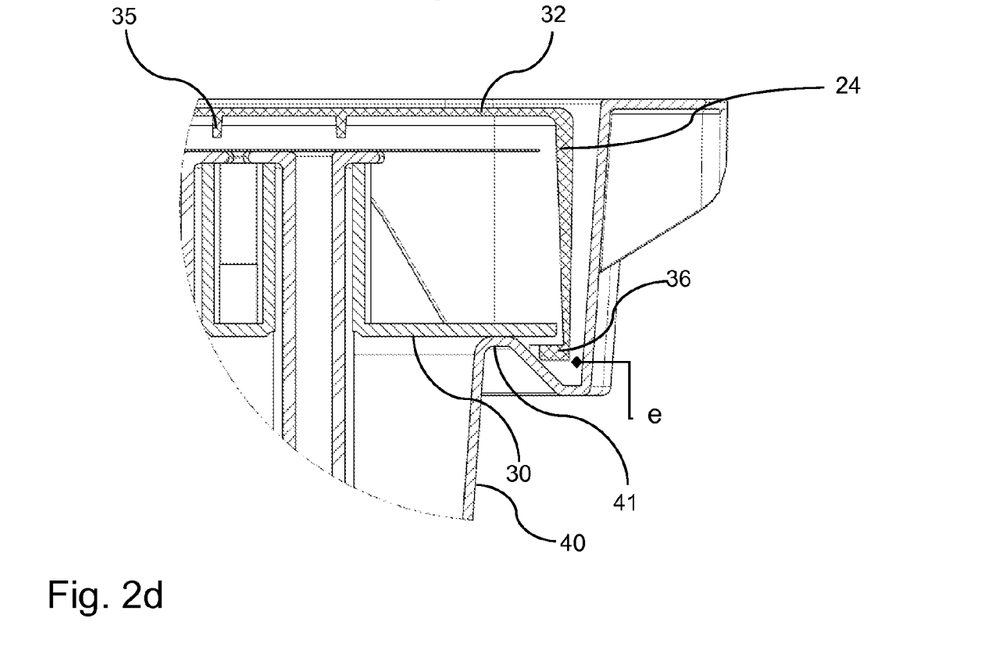

FIG. 2d shows that the tray 30 is supported on the top of the rib in the form of an inverted "U" 41. The cover 32 is supported on the outer side of the rib in the form of an inverted "U" 41, and leaves a space indicated by the letter "e" between the flank 24 of the cover and the lateral wall of the box, such that it is possible to put into place/remove the cover 32 when the tray 30 is in the box 40.

Figure 2E:
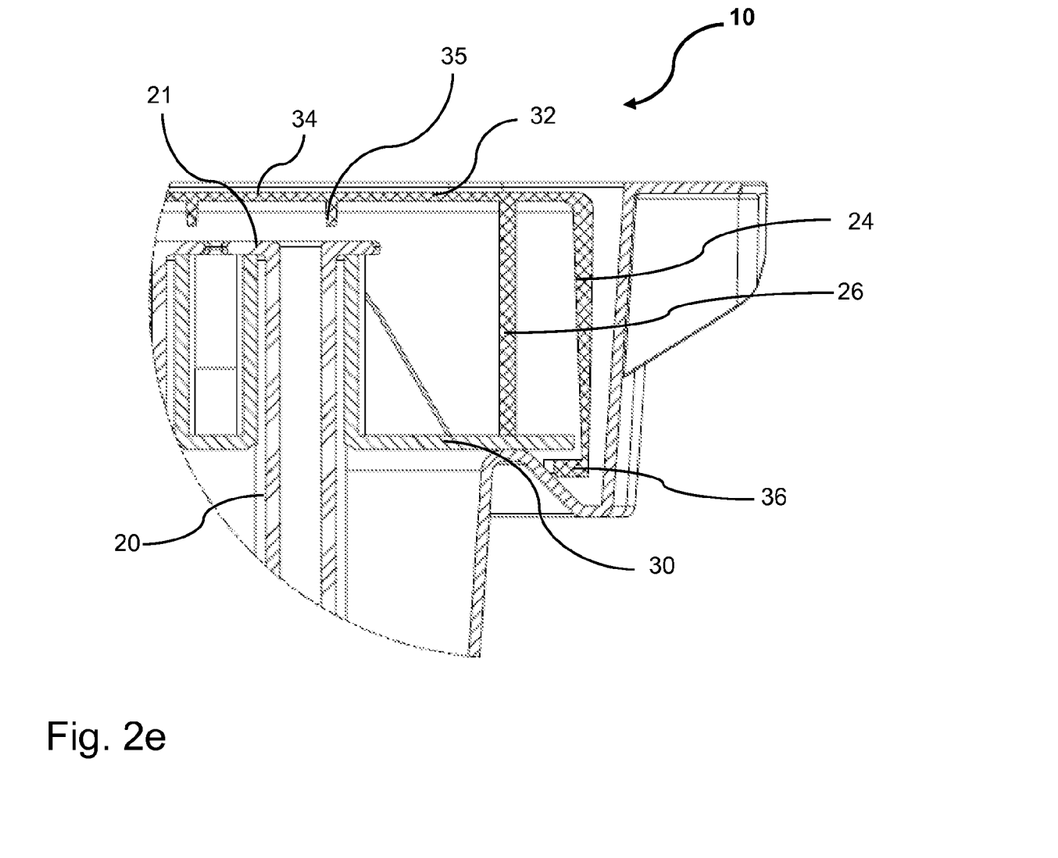
FIG. 2e is similar to FIG. 2d in a second embodiment of the invention.

According to a second embodiment of the invention, represented in FIG. 2e, the cover 32 additionally comprises support walls 26, 26' which are parallel to the flanks 24, 24', and are situated on the inner side of the latter. These support walls 26, 26' constitute a bearing for the cover 32 on the periphery of the tray 30. They have a height such that neither the upper wall 34 nor the ribs 35 are supported on the upper surface of the flanges 21 of the containers 20. It is thus possible to stack a number of packaging units 10, without risk of applying forces on the containers 20.

Figure 3A:
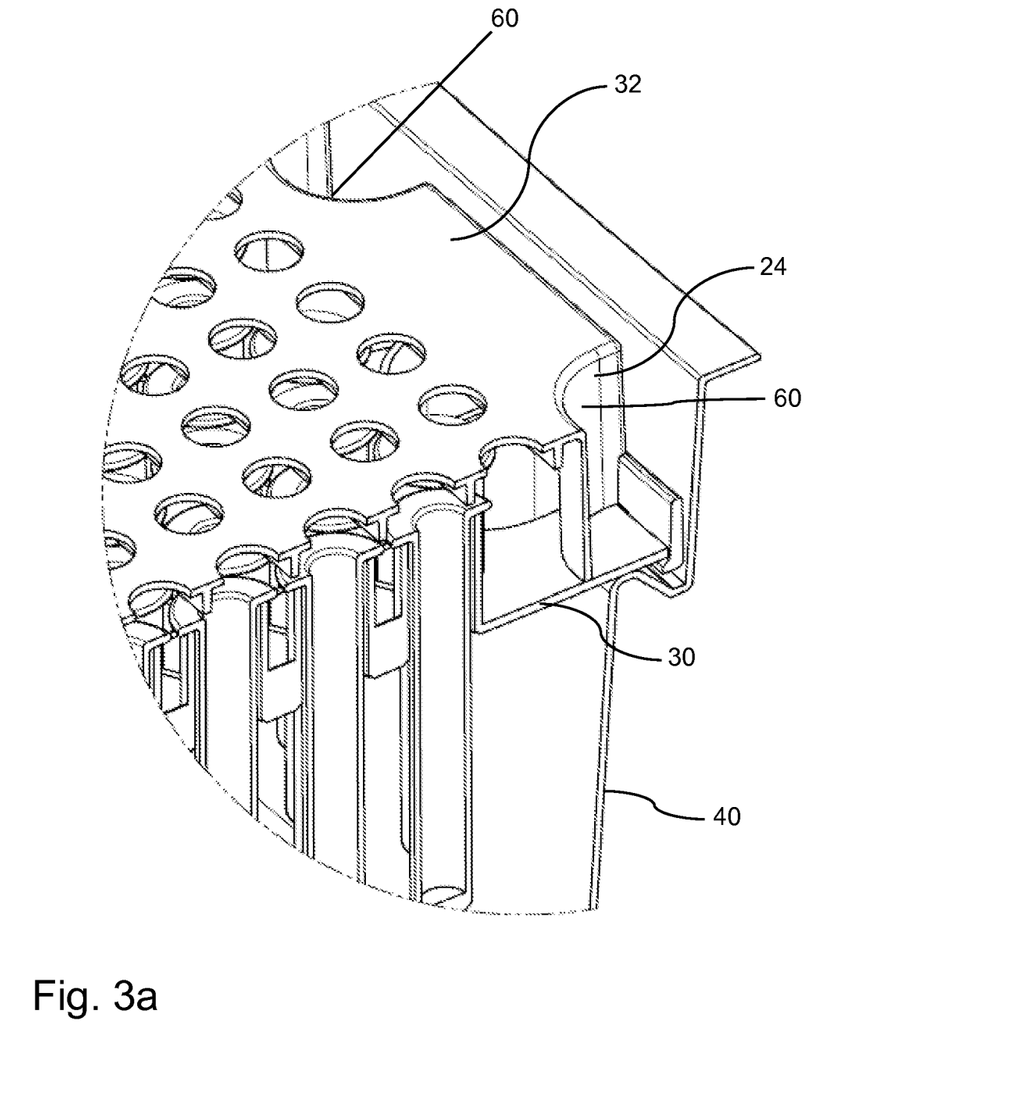
FIG. 3a is a view in isometric projection and in cross-section of part of a packaging unit according to a third embodiment of the invention.

FIG. 3a is a view in perspective and in cross-section of a packaging unit comprising a cover 32 according to a third embodiment of the invention. According to this mode, the flanks 24, 24' on two sides of the cover 32 are interrupted and placed at portions of tube 60. These portions of tube play the part of the support walls 26, 26' of the second embodiment: they permit the support of the cover 32 on the tray 30. An advantage of this third embodiment is that these portions of tube permit access from above to a portion of the upper surface of the tray 30. Automatic grasping means, which are provided for example with suckers, can then deposit the cover/tray assembly in a box 40, or remove it from a box 40.

Figure 3B:
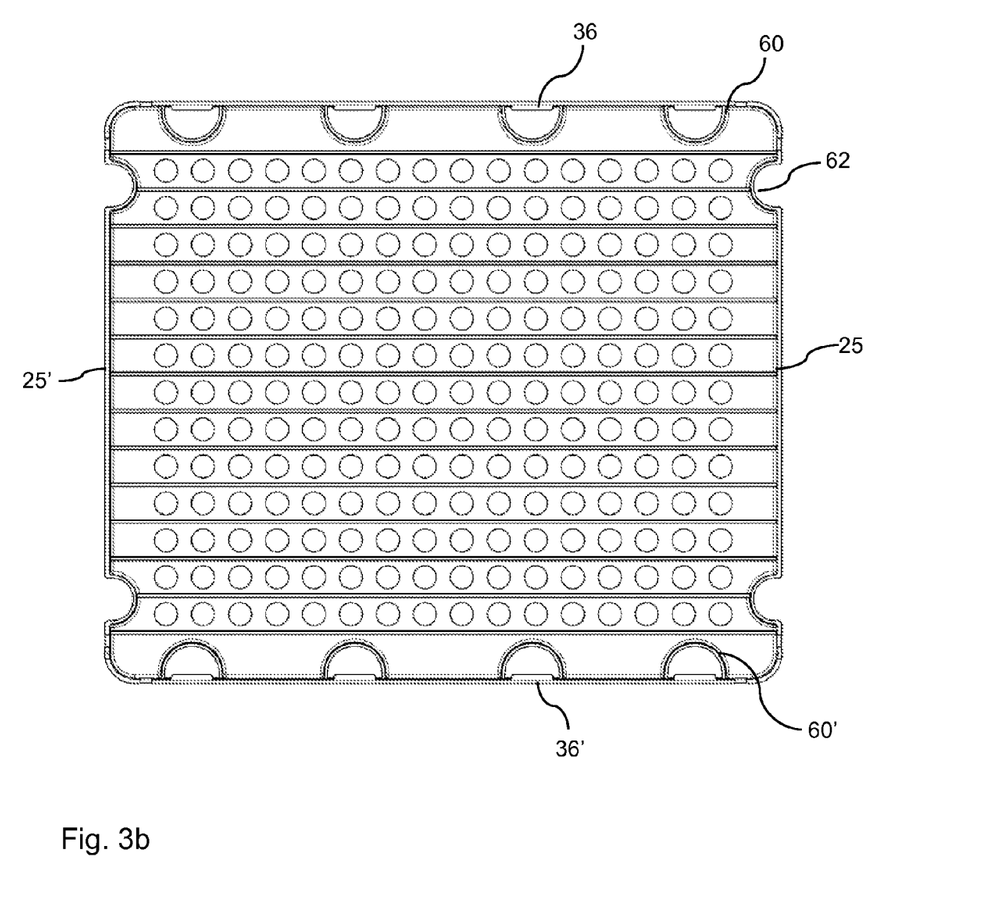
FIG. 3b is a view from below of a cover of a packaging unit according to this third embodiment.

FIG. 3b is a view from below of a cover 32 according to the third embodiment. Portions of tube 62 are also provided on the two other sides of the cover 32, which has the effect of facilitating the bending of the cover, despite the presence of flanks 25, 25' on these sides. The fingers 36, 36' are arranged at the level of the tubes of the portions of tube 60, 60', thus permitting creation of a mold which is simple to produce.

Figure 4A:
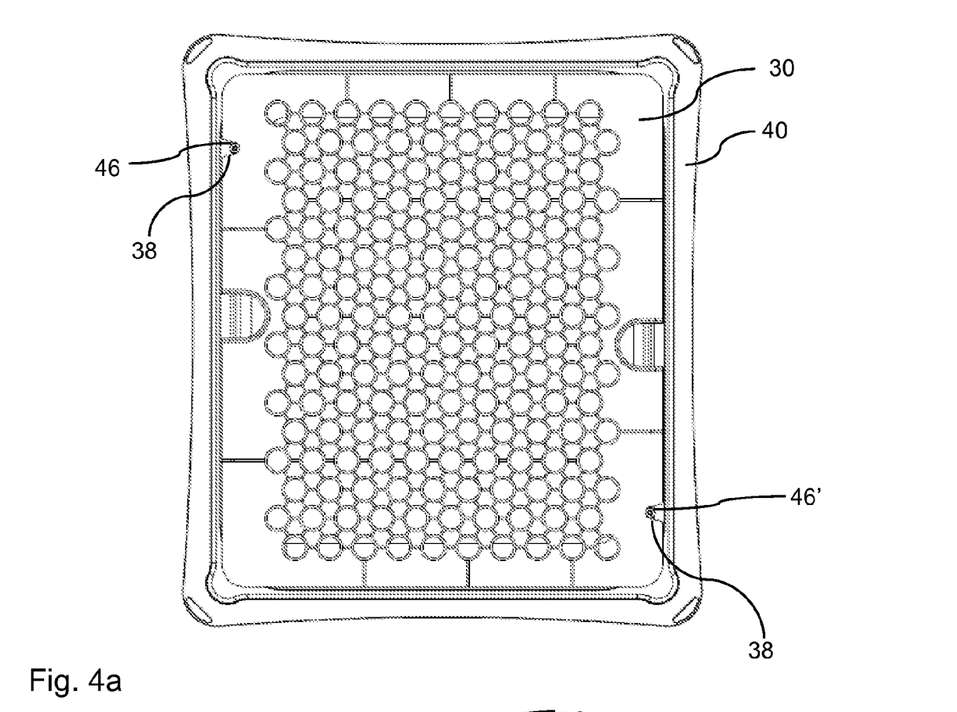
FIG. 4a is a plan view of a box containing a tray of a packaging unit according to the invention, and representing first means for immobilization of the tray.

FIG. 4a is a plan view of a box 40 containing a tray 30 of a packaging unit according to the invention, and shows the position of the means for immobilization of the tray 30 in the box 40. According to first means for immobilization, represented in FIGS. 4a and 4b, centering pins 46, 46' are provided on the step 45 of the box, and corresponding immobilization cut-outs 47, 47' are provided in the tray 30.

Figure 4B:
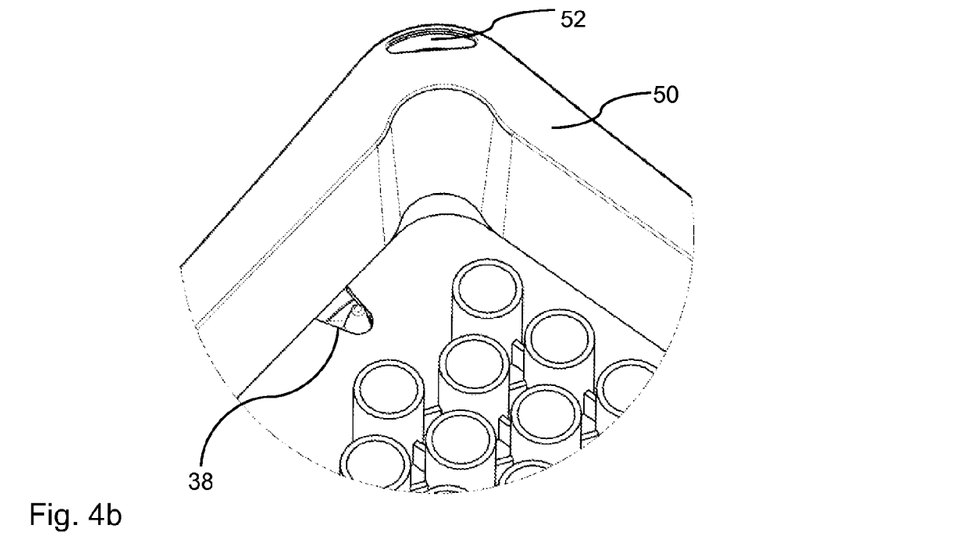
FIGS. 4b, 4c, 4d are enlarged views in perspective of a portion of the view in FIG. 4a, representing respectively first, second and third means for immobilization of the tray.

FIG. 2c is an enlarged view of the cross-section A-A which shows the centering pin 46. This FIG. 2c shows that this centering pin has a frustoconical form. In addition, FIGS. 4a and 4b show that the cut-out 47 has the form of a "V". These forms ensure firstly that when the tray is deposited in the box, the tray is centered automatically in the box. Secondly, these forms ensure clamping which prevents any movement which generates particles during storage and/or transport.

Figure 4C:
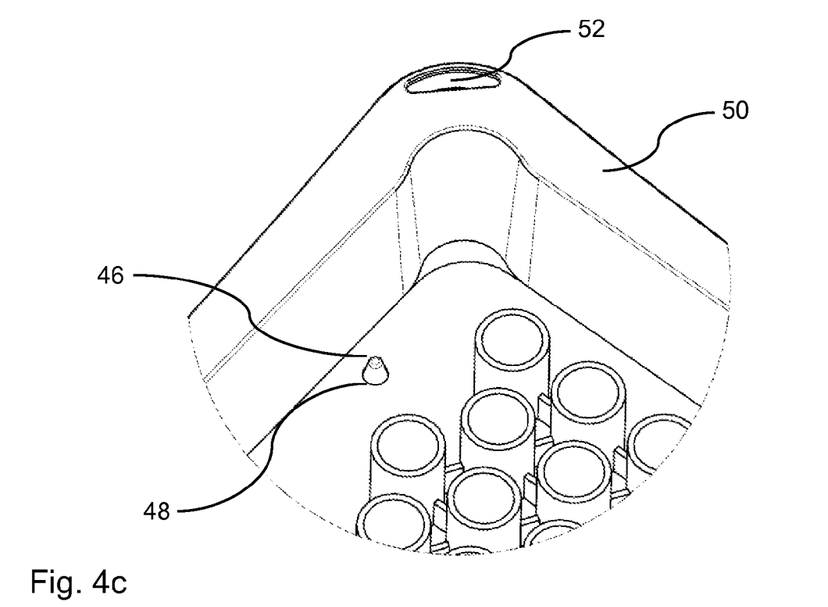

FIG. 4c represents second means for immobilization, wherein the immobilization cut-out 47 is replaced by a simple round hole 48 provided in the tray 30.

Figure 4D:
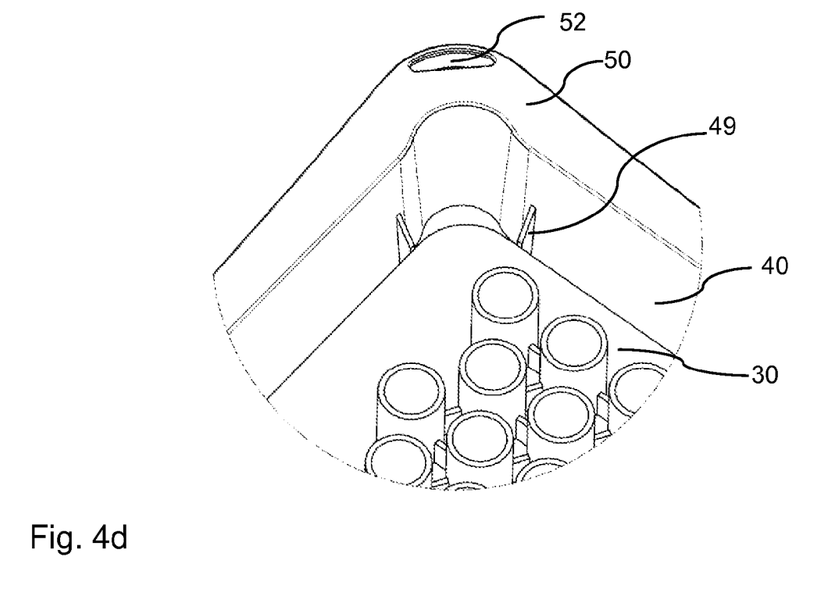

FIG. 4d represents third means for immobilization, wherein a rib 49 is placed vertically along the inner surface of the upper lateral wall of the box 40. This rib can advantageously have an inclined profile which guides the tray 30 progressively into position. These third means for immobilization have the advantage that they can be used with nest trays which are not modified, and which constitute an industrial standard.

Two means for immobilization are advantageously positioned on opposite sides and close to opposite angles of the box, as represented in FIG. 4a. The use of these means for immobilization ensures that a tray 30 positioned in a box 40 is located in a specific place, and has no degree of freedom. It is therefore not liable to be displaced during the transport and/or storage. This therefore prevents the creation of particles. In addition, the precise knowledge of the position of the tray 30 in the box 40 can facilitate certain operations such as filling of the containers and automatic grasping. It will be understood that it is possible to have two or more than two means for immobilization, and to combine the first, second and third means.

FIGS. 4a, 4b and 4c represent an optional characteristic of the box 40. In a box of this type, it is known to provide an upper rim 50, which permits gluing of a cap 12, represented in FIG. 1a. In a preferred embodiment of the invention, an opening 52 has been provided in at least one corner of this rim 50. This opening permits the flow of the condensed water vapor or the gas after the sterilization. In addition, it makes it possible to raise a cap 12 in order to be able to detach it easily.

As shown in an enlarged view in FIGS. 2c, 2d and 2e, the upper wall 34 of the cover 32 can comprise ribs 35 on its lower surface. These ribs make it possible to ensure the rigidity of the tray, and are preferably oriented parallel to the flanks 24, 24', so as to maintain a certain flexibility of the tray in the direction perpendicular to the flanks 24, 24'. Preferably, these ribs 35 are provided above the flanges 21 of the containers 20, in order to optimize the processes of sterilization of the syringes 20, as follows. Since the tray 30 can be overturned without allowing the syringes 20 to fall, it is possible to carry out the sterilization, such as the sterilization by steam, whilst keeping the syringes 20 in an overturned vertical position. The advantage of carrying out sterilization of the syringes in an inverted vertical position is to prevent the accumulation of condensation water in the syringes. The residues of sterilization gas can also be discharged. Said ribs 35 separate the flanges 21 of the inverted syringes 20 from the upper wall 34 of said tray 30, which has the consequence that the sterilization is more efficient, since the steam or gas can easily reach the inner parts of the syringe 20.

Figure 6:
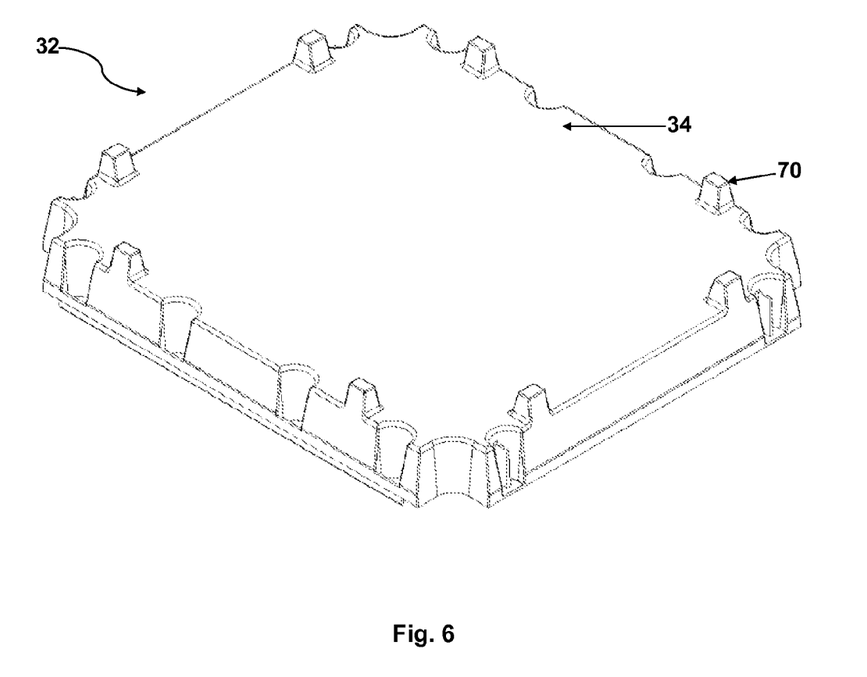
FIG. 6 represents a view in perspective of a cover comprising means for positioning a second packaging unit according to an embodiment of the invention.

FIG. 6 represents a view in perspective of a cover 32 according to a particular preferred embodiment of the invention. The cover 32 additionally comprises on its upper wall 34 a positioning means 70 of a second packaging unit 10'

(not represented). As represented in FIG. 6, the positioning means 70 can be a projection or a pin. A plurality of pins or projections can be arranged on the upper wall 34 of the cover 32, in order to stabilize the second packaging unit 10' positioned on said cover 32. Thus, a plurality of packaging units 10, 10' can be stacked, but maintain the stability necessary in order to prevent any risk during their transport. Alternatively, the positioning means 70 can be a continuous skirt arranged on the periphery of the upper wall 34.

By means of its cover, the packaging unit according to the invention makes it possible to avoid any direct contact with the containers and their flanges. It makes it possible to stack packaging units at various stages of their production, transport and checking. It also makes it possible to sterilize the containers after they have been filled ("post-sterilization") without needing to dismantle/reassemble packaging units. The production of the cover has a low cost, particularly when it is produced by injection of a polymer in a simple mold. A cover can therefore be provided for each container, and used throughout the production chain.

Figure 5:
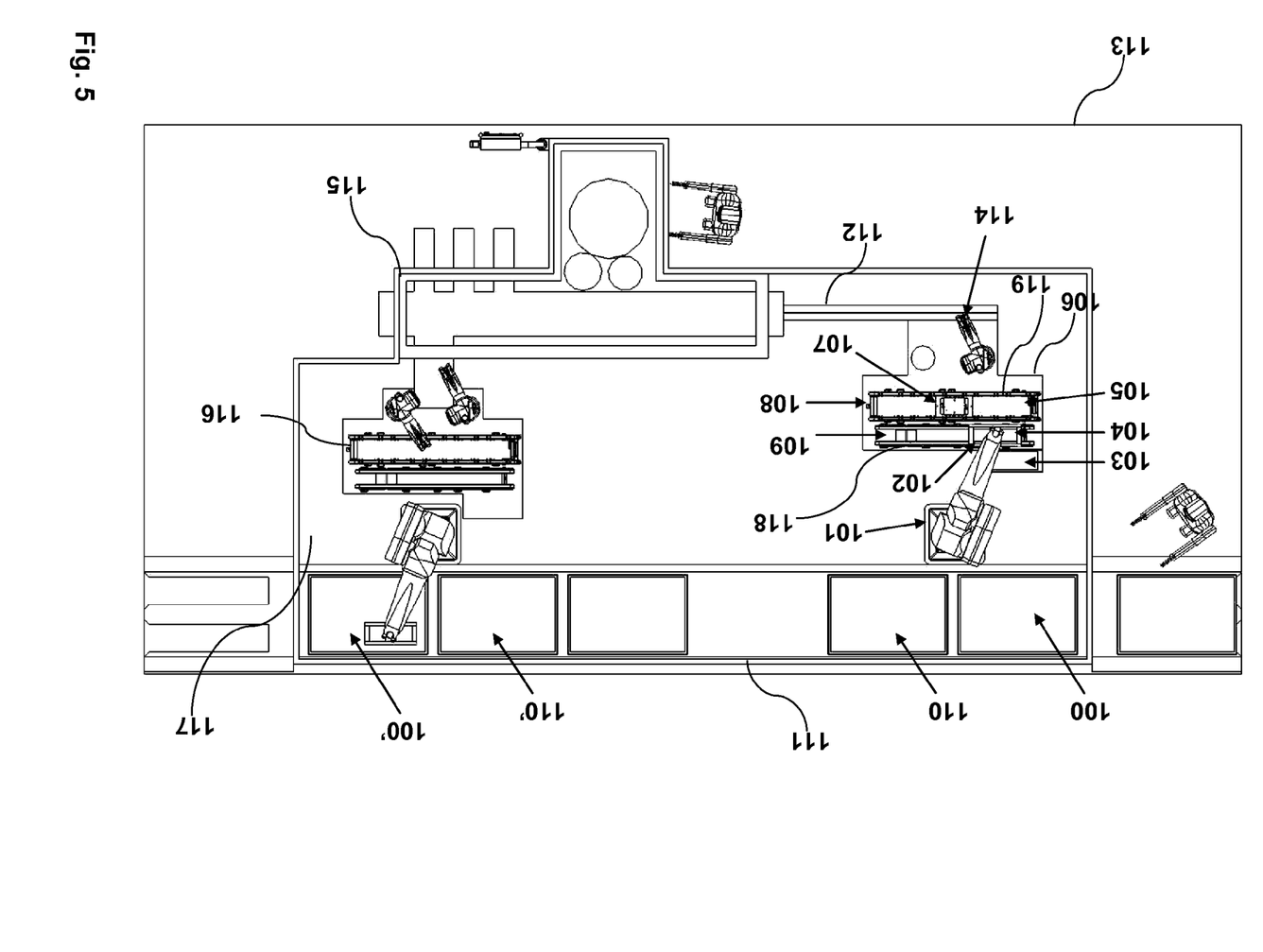
FIG. 5 represents a schematic view of an area of handling of a packaging unit according to an embodiment of the invention.

FIG. 5 represents a schematic view of an area of handling of a packaging unit according to an embodiment of the invention. The area of handling 113 can for example be an area of optical inspection of objects 20 contained in a tray 30, or an area of filling of the objects 20 with a solution containing a therapeutic agent. This area of handling 113 comprises in particular a pallet conveyor 111, on which full 100, 100' and/or empty 110, 110' pallets are conveyed, a first grasping robot 101, a de-nesting device 106 and a conveyor 112 for objects 20. "De-nesting" means the operation of dismantling a packaging unit 10 in order to obtain objects 20 separated from the other elements which constitute the packaging unit 10. The de-nesting device 106 can comprise a store of covers 103, a conveyor 118 for boxes 40, a conveyor 119 for trays 30, and a de-nesting unit 107. The de-nesting device 106 makes it possible to separate the component elements of a packaging unit 10, irrespective of the type of tray used. The de-nesting unit 107 makes it possible to remove the objects 20 from the tray 30, whether the latter is a tray of the nest or comb type. Thus, at the output from the de-nesting device 106, the objects 20 are conveyed by means of a second grasping robot 114 and an object conveyor 112 to a second processing area 115, such as, for example, an optical inspection area.

According to a particular embodiment of the invention, the packaging units 10 according to the invention, arranged in the pallet 100, comprise a tray 30 which supports objects 20, a box 40 and a cover 32 as previously described (not represented in FIG. 5). In particular, the cover 32 has on two sides flanks 24, 24' which are interrupted and placed at portions of tube 60, as represented in FIG. 3a. These portions of tube 60 permit the support of the cover 32 on the tray 30. The cover also comprises portions of tube 62 on the two other sides, thus facilitating the bending of the cover.

An empty pallet 110 is placed at the entry of the conveyor 111, then displaced opposite the first grasping robot 101. A full pallet 100 comprising a plurality of packaging units 10 is placed at the entry of the conveyor 111, then placed opposite the first grasping robot 101, as represented in FIG. 5. The term "opposite the first grasping robot 101" means that said pallets 110 and/or 100 are within a perimeter which allows said first grasping robot 101 to carry out one or more handling operations on them. For example, the first grasping robot 101 can thus take a packaging unit 10 from the full pallet 100, or deposit a packaging unit 10 in an empty pallet 110. According to one embodiment, the first grasping robot 101 seizes one or more packaging units 10 by means of its grasping unit 102. Preferably, the first grasping robot 101 seizes two packaging units 10, 10' simultaneously. Said one or more packaging units 10 is/are displaced towards the de-nesting device 106, where the separation of the component elements of the packaging unit 10 takes place. The following steps of the separation process will be described considering that the grasping robot 101 handles two packaging units 10 and 10' simultaneously. It is apparent from reading the description that the following steps of the process can also be carried out when the first grasping robot 101 handles a single packaging unit 10, or more than two packaging units 10, for example three, four, five or six packaging units simultaneously.

The packaging units 10, 10' (not represented in FIG. 5) which are seized by the grasping robot 101 are displaced vertically relative to the first end 104 of the conveyor 118. The boxes 40, 40' of said packaging units 10, 10' are deposited on the conveyor 118 at the level of said end 104. The separation of the boxes 40, 40' from the remainder of the packaging units 10, 10', i.e. from the integral assembly formed by a tray 30 and a cover 32, is carried out by the grasping unit 102 of said first grasping robot 101. The grasping unit 102 can impose pressure on the lateral surface of the boxes 40, 40', and thus assist the separation of said boxes 40, 40' from the cover/tray assemblies 32, 30 and 32', 30'. By means of the presence of the portions of tube 60 on each of the covers 32, 32' of each of the packaging units 10, 10', the first grasping robot 101 can gain access to a portion of the upper surface of the trays 30, 30', and thus retain the cover/tray assemblies 32, 30 and 32', 30' integrally. The grasping unit 102, which is provided for example with suckers, can seize, for each of the packaging units 10, 10', the cover/tray assemblies 32, 30 and 32', 30', and separate these from the boxes 40, 40'. This step is carried out with a single grasping robot 101, unlike the process according to the prior art. In fact, the packaging units which are used at present comprise a cover provided with fingers which are secured below the rim of the packaging unit box. This configuration requires the use of a second robot or manual handling, in order to hold the box while the cover is removed. Said boxes 40, 40' can be arranged on a first mobile support which can displace the boxes on the conveyor 118 of the first end 104 and the second end 109.

The cover/tray assembly 32, 30 of each of the packaging units 10, 10' is placed vertically relative to the first end 105 of the conveyor 119. The trays 30, 30' are arranged on the conveyor 119 at the level of the first end 105. The trays 30, 30' can be arranged on a second mobile support which can displace the trays along the conveyor 119 of the first end 105 and the second end 108. The action of the grasping unit 102 of said first grasping robot 101 makes it possible to separate the covers 32, 32' from the trays 30, 30' by the imposition of curvature in the form of a "U" on each of the upper walls of the covers 32, 32'. The trays 30, 30' are thus separated from the covers 32, 32'. The covers 32, 32' can be displaced vertically relative to the cover store 103, and deposited inside the latter by the grasping unit 102 of the first grasping robot 101. During the processing of a pallet 100 comprising more than four packaging units, only the first four covers 32 obtained from the first four packaging units 10 are arranged inside the cover store 103. In the other cases, the grasping unit 102 which retains the covers 32, 32' is positioned vertically relative to the second end 108 of the tray conveyor 119.

The steps aimed at the removal of the objects 20, 20' contained respectively in the trays 30, 30' are then begun. The boxes 40, 40' which are arranged at the first end 104 of the box conveyor 118 are displaced towards the second end 109 of this same conveyor 118. The trays 30, 30' which are positioned at the level of the first end 105 of the tray conveyor 119 are displaced at the level of the de-nesting unit 107. The objects 20, 20' are removed from the trays 30, 30' at the level of this de-nesting unit 107. The objects 20, 20' can be taken over by a second grasping robot 114, and arranged on an object conveyor 112. The empty trays 30, 30' are then displaced from the de-nesting unit 107 towards the second end 108 of the tray conveyor 119. The trays 30, 30' are thus situated plumb with the grasping unit 102 which contains the covers 32, 32'. However, for the last four packaging units of the pallet 100 processed in the handling area 113, the first grasping robot 101 is positioned vertically relative to the cover store 103, in order to seize two covers 32, 32', and is then positioned vertically relative to the second end 108 of the conveyor 119. The trays 30, 30' are assembled with the covers 32, 32'. The assembly is carried out by means of the grasping robot 101 and its grasping unit 102. Said grasping unit 102 imposes curvature or deformation on the upper walls of the covers 32, 32', thus allowing the fingers 36, 36' which are situated at the lower ends of the flanks 24, 24' of each of the covers 32, 32' to be placed below a lower surface of said trays 30, 30', thus rendering the trays 30, 30' and the covers 32, 32' respectively integral with one another. Said grasping unit 102 thus retains the tray/cover assemblies 30/32 and 30'/32' by means of their respective portions of tube 60. The grasping unit 102 is positioned vertically relative to the second end 109 of the conveyor 118, and assembles the tray/cover assemblies 30/32 and 30'/32' respectively with the boxes 40 and 40'. The packaging units 10, 10' with the objects 20, 20' emptied from them are thus reconstituted. The packaging units 10, 10' with the objects 20, 20' emptied from them are displaced vertically relative to the pallet conveyor 111, then deposited in an empty pallet 110.

Alternatively, according to another embodiment of the invention, the box conveyor 118 can be replaced by a box store. The boxes 40 are thus deposited on a non-mobile surface of the de-nesting device 106. When the operations of emptying or assembly of the tray have been carried out, the grasping robot positions the tray/cover assembly 30/32 in the corresponding box, seizes the latter, and displaces it towards the pallet conveyor 111, in order to position it inside a pallet 110.

The operations can be repeated until all the packaging units 10 have been emptied from the full pallet 100. As represented in FIG. 5, the pallet 110 can be displaced by the pallet conveyor 111 into a preparation area 117, and put into position 110'. This pallet 110' thus comprises packaging units 10, wherein the objects 20 have been emptied from the tray 30. The method for separation as previously described can also be carried out in the preparation area 117. Only the de-nesting unit 107 of the de-nesting device 106 can be replaced by a device 116 for assembly of the objects 20 in the tray 30, thus carrying out the operations which are the inverse of the de-nesting operation. The pallet 100' is thus filled with the packaging units 10 comprising objects 20 which are retained in a vertical position in the tray 30.

The terms and descriptions used here are proposed solely by way of illustration, and do not constitute limitations. Persons skilled in the art will recognize that many variations are possible within the spirit and scope of the invention as described in the following claims and their equivalents; in the claims, all the terms must be understood according to their most widely accepted meaning, unless otherwise indicated.

The invention claimed is:

1. A packaging unit for the storage and/or transport and/or processing and/or support in a suspended vertical position, of syringes which have flanges, said packaging unit comprising
 a tray configured to fit inside a box, the tray having means to retain a plurality of said syringes in a vertical position, wherein the tray has a lower surface, an upper surface, and a periphery and the lower surface is substantially flat along the periphery; and
 a cover which can cover said tray,
 wherein said cover comprises an upper wall and at least two flanks which extend downwards on two opposite side of the upper wall, each of the flanks being prolonged at its lower end by fingers which can be placed below the lower surface of said support plate, thus rendering the tray and the cover integral; said upper wall has flexibility which makes it possible for it to be curved, such as to space one finger from an opposite finger, and thus to allow these fingers to be placed below the lower surface of said tray.

* * * * *